United States Patent
Kudavelly et al.

(10) Patent No.: US 9,597,054 B2
(45) Date of Patent: Mar. 21, 2017

(54) ULTRASONIC GUIDANCE OF A NEEDLE PATH DURING BIOPSY

(71) Applicant: KONINKLIJKE PHILIPS N.V., Eindhoven (NL)

(72) Inventors: Srinivas Rao Kudavelly, Eindhoven (NL); Raja Sekhar Bandaru, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 256 days.

(21) Appl. No.: 14/368,527

(22) PCT Filed: Jan. 17, 2013

(86) PCT No.: PCT/IB2013/050417
§ 371 (c)(1),
(2) Date: Jun. 25, 2014

(87) PCT Pub. No.: WO2013/108198
PCT Pub. Date: Jul. 25, 2013

(65) Prior Publication Data
US 2014/0350390 A1    Nov. 27, 2014

Related U.S. Application Data

(60) Provisional application No. 61/587,784, filed on Jan. 18, 2012.

(51) Int. Cl.
*A61B 8/00*    (2006.01)
*A61B 8/08*    (2006.01)
*A61B 10/02*   (2006.01)

(52) U.S. Cl.
CPC .......... *A61B 8/0841* (2013.01); *A61B 8/0858* (2013.01); *A61B 8/463* (2013.01);
(Continued)

(58) Field of Classification Search
CPC ....... A61B 8/463; A61B 8/08; A61B 17/3403; A61B 17/3462; A61B 17/3494; A61B 2017/3492; A61B 3017/3405
See application file for complete search history.

(56) References Cited

U.S. PATENT DOCUMENTS 5,997,479 A    12/1999   Savord et al.
6,013,032 A    1/2000    Savord
(Continued)

FOREIGN PATENT DOCUMENTS

EP    1649818 A2      4/2006
WO    01/78607 A1     10/2001
WO    2007059452 A2   5/2007

*Primary Examiner* — Joel Lamprecht

(57) ABSTRACT

An ultrasonic imaging system is described which visually assists biopsy needle insertion. The system produces pixel values of pixels along one or more paths of needle insertion. A tissue density analyzer is responsive to the pixel values to estimate tissue density along a path of needle insertion. A needle path calculator is responsive to the tissue density analyzer and proposes one or more favorable paths through imaged tissue for insertion of the biopsy needle. The system may be used in conjunction with a three dimensional navigation system which spatially locates the needle and ultrasound image plane in 3D space.

15 Claims, 4 Drawing Sheets

(52) U.S. Cl.
CPC ........ *A61B 8/5207* (2013.01); *A61B 10/0233* (2013.01); *A61B 8/483* (2013.01); *A61B 90/11* (2016.02); *A61B 2034/107* (2016.02); *A61B 2090/378* (2016.02)

(56) References Cited

U.S. PATENT DOCUMENTS

| | | | |
|---|---|---|---|
| 6,351,660 | B1 | 2/2002 | Burke |
| 6,368,281 | B1 | 4/2002 | Solomon et al. |
| 6,419,633 | B1 | 7/2002 | Robinson et al. |
| 6,497,663 | B2 | 12/2002 | Fraser et al. |
| 7,452,357 | B2 * | 11/2008 | Vlegele .................. A61B 90/10 600/439 |
| 2006/0089626 | A1 | 4/2006 | Vlegele |
| 2008/0091103 | A1 | 4/2008 | Sundar et al. |
| 2009/0306511 | A1 * | 12/2009 | Yamagata ............ A61B 8/0833 600/447 |
| 2011/0137156 | A1 * | 6/2011 | Razzaque .......... A61B 19/5244 600/424 |

* cited by examiner

ULTRASONIC GUIDANCE OF A NEEDLE PATH DURING BIOPSY

This application is the U.S. National Phase application under 35 U.S.C. §371 of International Application No. PCT/IB2013/050417, filed on Jan. 17, 2013, which claims the benefit of U.S. Provisional Application No. 61/587,784 filed on Jan. 18, 2012. These applications are hereby incorporated by reference herein.

This invention relates to medical diagnostic imaging systems and, in particular, to diagnostic ultrasound systems which provide visual guidance of a needle during biopsy or other invasive procedure.

A biopsy is a medical procedure involving the removal of cells or tissues for examination. The procedure comprises the medical removal of tissue from a living subject to determine the presence or extent of a disease. The excised tissue is generally examined under a microscope by a pathologist, and can also be analyzed chemically for disease states. When an entire lump or suspicious area is removed, the procedure is called an excisional biopsy. When only a sample of tissue is removed with preservation of the histological architecture of the cells of the tissue, the procedure is called an incisional biopsy or core biopsy. When a sample of tissue or fluid is removed with a needle in such a way that cells are excised without preserving the histological architecture of the tissue cells, the procedure is called a needle aspiration biopsy.

In order to efficiently insert the needle directly to the target tissue it is preferable to perform the procedure with the assistance of diagnostic imaging such as ultrasound imaging. The clinician can locate the target tissue in the image, then insert the needle in line with the image plane. The clinician can then observe the needle as it is inserted and confidently guide the needle until the needle tip accesses the target tissue. A sample of the target tissue can then be aspirated or excised through the needle. For even greater ease and precision, the procedure can also use a surgical navigation system such as the Philips PercuNav guidance system. The PercuNav system broadcasts a modulated magnetic field around and through the site of the procedure. Sensors are positioned on the needle and the ultrasound imaging probe so that the system can locate the position and orientation of the patient, the surgical site, the needle and the ultrasound image plane in three dimensional space. The PercuNav system can then aid in the more precise display of the needle and needle tip in the ultrasound image and its position and orientation with respect to the image plane. The clinician can indicate the target tissue on the ultrasound image and the PercuNav system will graphically indicate on the display the path to be followed by the needle to reach the target tissue.

However, difficulties in tumor targeting still exist as the ultrasound image plane and biopsy needle must remain coplanar throughout the procedure to display the actual needle tip position. Also, the Philips PercuNav system will not suggest a favorable path for insertion which provides the least resistance to insertion and avoids nearby sensitive organs. In many instances the needle will deflect and bend as it encounters stiff or dense tissue during insertion. As a result, biopsy procedural efficiency is hindered since needle pathway interpretation is often difficult, especially for needle insertions at large depths that can require multiple reinsertions. All the aforementioned difficulties result in additional time with multiple reinsertions of the biopsy needle with increased patient discomfort and morbidity. Accordingly it is desirable for the imaging system to predict the most favorable path for needle insertion so as to reduce technique variability and unnecessary injury to the patient. This will lead to a shorter learning curve for biopsy procedures, reduce procedure time, avoid multiple biopsy needle insertions and enable consistent replicable biopsy procedures, thereby reducing discomfort to the patient and improving outcomes.

In accordance with the principles of the present invention, an ultrasonic imaging system is provided for guiding needle insertion procedures. An ultrasound probe images the target tissue for the procedure and the tissue through which the needle is inserted to access the target tissue. As the insertion begins, ultrasonic echo information of pixels along the projected insertion path is acquired and analyzed to determine local variations in tissue density along the projected path. If the analysis shows that a region of dense tissue will be encountered along the intended path, densities along other possible paths are acquired and analyzed and an alternative insertion path is presented for consideration by the clinician. The clinician can then choose an insertion path which is most effective for the procedure and most comfortable for the patient.

Figure 1:
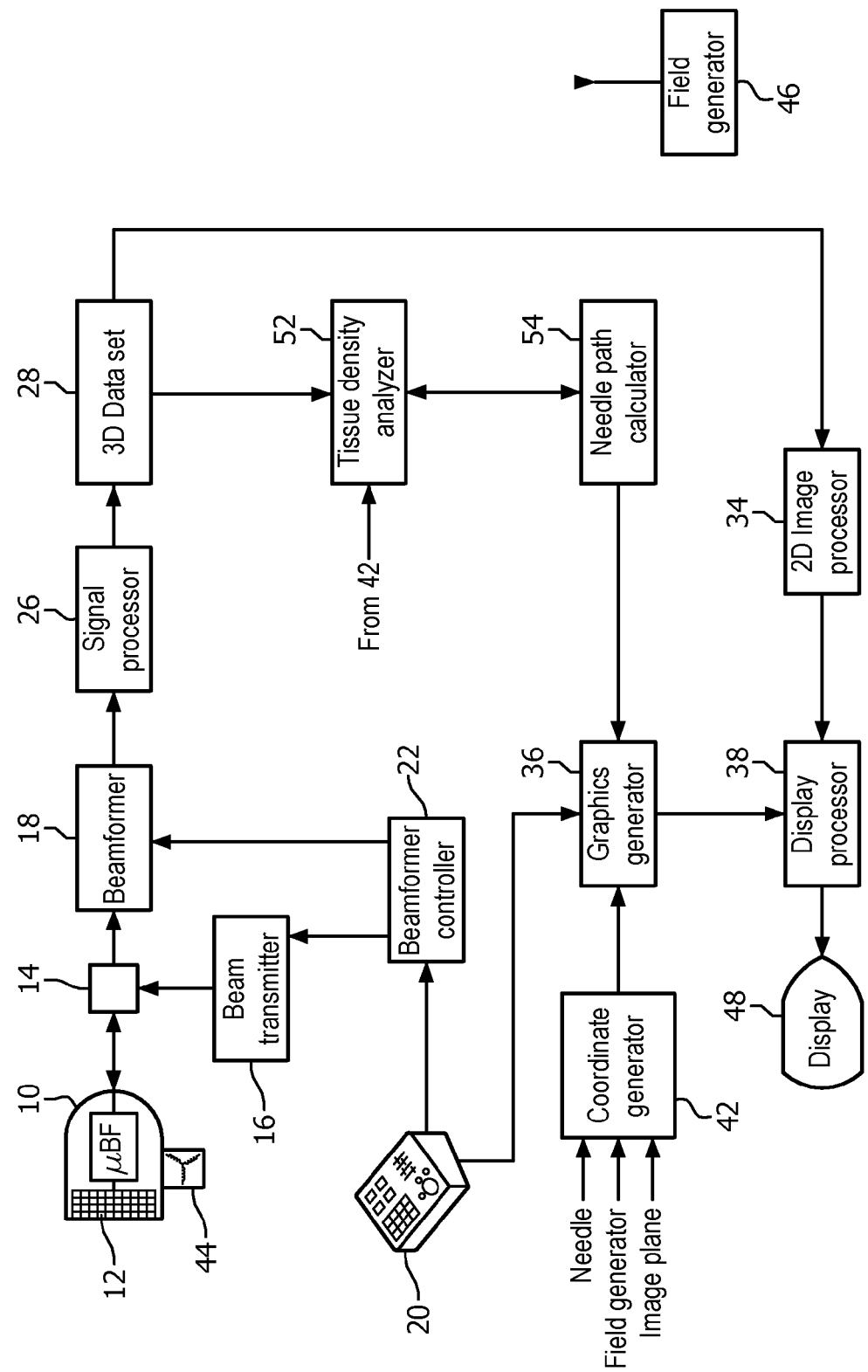
FIG. 1 illustrates in block diagram form an ultrasonic imaging system for needle guidance constructed in accordance with the principles of the present invention.
Figure 3:
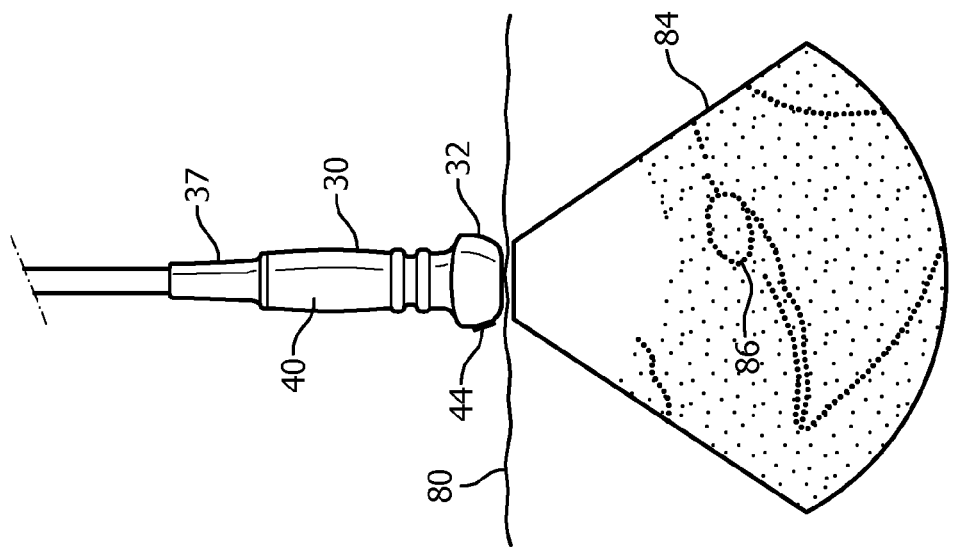
FIG. 3 illustrates an ultrasound probe imaging target tissue and tissue through which the target is accessed in a body.

Referring first to FIG. 1, an ultrasonic imaging system for assisting needle guidance is shown in block diagram form. an ultrasound probe 10 contains an array transducer 12 for scanning and imaging the region in front of the transducer. The transducer array can be a one-dimensional (1D) array for scanning a plane in front of the probe, but preferably the transducer is a two dimensional (2D) array transducer 12 which transmits electronically steered and focused beams over a volumetric region and receives single or multiple receive beams in response to each transmit beam. With the 2D array 12 the probe can scan an image plane and the tissue on either elevational side of the image plane. Groups of adjacent transducer elements of the array, referred to as "patches" or "subarrays," are integrally operated by a microbeamformer (μBF) in the probe 12, which performs partial beamforming of received echo signals and thereby reduces the number of conductors in the cable between the probe and the mainframe ultrasound system. Suitable two dimensional arrays are described in U.S. Pat. No. 6,419,633 (Robinson et al.) and in U.S. Pat. No. 6,368,281 (Solomon et al.) Microbeamformers are described in U.S. Pat. No. 5,997,479 (Savord et al.) and U.S. Pat. No. 6,013,032 (Savord). The transmit beam characteristics of the array are controlled by a beam transmitter 16, which causes the apodized aperture elements of the array to emit a focused beam of the desired breadth in a desired direction through a volumetric region of the body. Transmit pulses are coupled from a beam transmitter 16 to the elements of the array by means of a transmit/receive switch 14. The echo signals received by the array elements and partially beamformed by the microbeamformer in response to a transmit beam are coupled to a system beamformer 18, where the partially beamformed echo signals are processed to form fully beamformed single or multiple receive beams in response to a transmit beam. A suitable beamformer for this purpose is described in the aforementioned Savord '032 patent.

The receive beams formed by the beamformer 18 are coupled to a signal processor 12 which performs functions such as filtering and quadrature demodulation. The echo signals along the receive beams are detected and processed into a succession of pixels along each beam which are stored as a 3D data set 28. A B mode ultrasound image is generally formed by pixels in a range of grayscale values which are proportionate to the strength of received echo signals. Blood and very soft tissue will return relatively weak echo signals which produce relatively low grayscale values that are presented as darker shades in a B mode image. The blood in a blood vessel will be reproduced as a dark, almost black shade. But hard and dense substances such as hard cysts and dense tissue and specular reflectors will return relatively strong echo signals. The pixels of relatively high pixel values displayed from these locations are displayed as bright, almost white pixels. Boundaries between different tissue types such as the boundaries of organs will also return strong echo signals which are displayed as bright pixels. Thus the values of the pixels are indicators of local tissue densities and organ boundaries.

The pixels of a plane of the scanned volume are coupled to a 2D image processor 34 where they are processed to form a two-dimensional ultrasound image of a scan plane of the volume. A technique for forming a 2D image from a 3D data set is commonly known and multi-planar reformatting (MPR). The MPR technique addresses the data values of image data which is in a common plane, which is then processed to form a 2D image of the selected plane. Alternatively, a plane of the scanned volume can be separately scanned in a time-interleaved manner as described in U.S. Pat. No. 6,497,663 (Fraser et al.), which can result in a 2D display with a higher frame rate. A control panel 20 by which the clinician controls the operation of the ultrasound system includes a control by which the clinician selects and positions the plane of the MPR or scanned 2D image. The 2D image plane is generally aligned with the center of the two-dimensional array transducer, which advantageously means that regions on both sides of the image plane are scanned to produce pixel values in the image plane and on either side of it in the elevation dimension. However, a plane which is offset from the center of the transducer can also be used in accordance with the present invention, and the plane can be orthogonal to the transducer or tilted at a non-orthogonal angle to the transducer array. The processed 2D image is coupled to the display processor where it is overlaid with graphics from a graphics generator 36, then displayed on the image display 48.

The ultrasound system described above can be used with a navigation system such as the PercuNav system, elements of which are shown in FIG. 1. The PercuNav system has a field generator 46 which radiates an electromagnetic field permeating the site of the procedure and surrounding space. Sensors 44 are located on the probe 10, the biopsy needle (not shown) and the patient (not shown) which interact with the electromagnetic field and produce signals used to calculate the position and orientation of the 2D image plane of the probe, the biopsy needle and needle tip, and the patient. This calculation is done by a coordinate generator 42 of the PercuNav system, which is shown receiving signals from the needle and image plane and is also coupled to the field generator for field registration purposes. Coordinate information of the needle and image plane is coupled to the graphics generator 36 which produces needle path graphics in response thereto and in response to operator control signals from the control panel 20 as described below.

Figure 2:
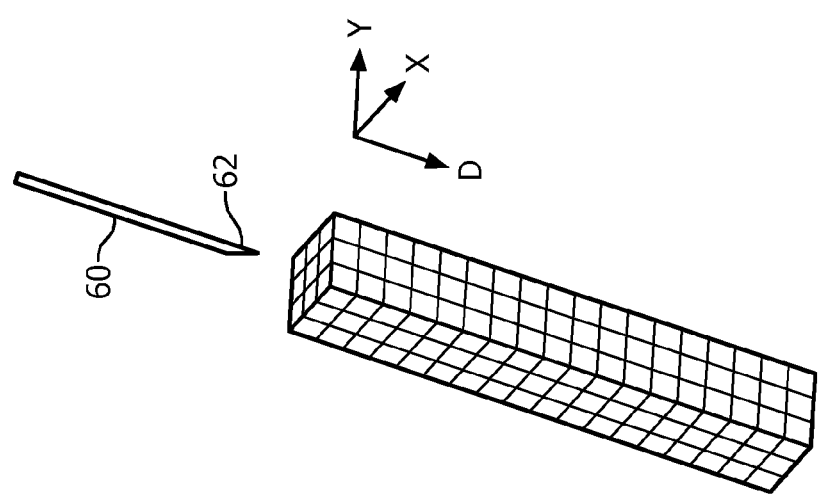
FIG. 2 illustrates a column of pixels along the projected insertion path of a biopsy needle.

In accordance with the principles of the present invention, a tissue density analyzer 52 is provided which receives pixel data of the 3D Data Set 28. Using the coordinate information of the projected path of needle insertion from coordinate generator 42, the tissue density analyzer selects out and analyzes pixels along the projected needle path. These pixels can all be in the same plane such as the plane of the 2D image produced by the 2D image processor 34. Preferably the pixels are a three dimensional set of pixels (voxels) of the 3D Data Set as illustrated in FIG. 2. This drawing illustrates a 3×3×N group of pixels where N is a number of pixels occupying some or all of the distance between the tip 62 of the needle 60 in the D direction. In this example the tip of the needle is aligned with the center column of this group of pixels which is in alignment with the projected path of the needle. This center column is surrounded in all directions by eight adjacent columns of pixels. Thus, each group of pixels in the x-y plane includes a center pixel on the projected needle path and pixels from the space surrounding the path. While a single column of pixels can be used, a three dimensional group is preferred as it samples the needle path and the pixel space around the path. In this example the tissue density analyzer 52 averages or sums the values of the nine pixels in each x-y plane and produces a value representing the tissue density at the distance D of the group along the needle path. For example, if there is dense, highly reflective anatomy at a given pixel plane, the value of the combined pixels of that location along the path will be relatively high, indicating a dense substance which may impede needle insertion. An organ boundary along the path will also generally return stronger echo signals. If a location comprises only soft tissue, the combined value will be relatively low, indicating less dense substance which should be easily penetrated by a needle. The sequence of density estimates thus calculated in the D direction is forwarded to a needle path calculator 54. The tissue density analyzer also performs this operation for possible needle paths adjacent to the projected needle path. For example the calculation can be performed on another group of pixels with the same y and D coordinates but with x incremented by three, identifying a similar 3×3×N group of pixels immediately adjacent to the first one. A sequence of density estimates is similarly calculated for this adjacent group of pixels. An adjacent but non-parallel group can be addressed by using incrementally different x coordinates along the D direction, which would provide a density estimate for a possible insertion path adjacent to but not parallel to the initial projected path. When the needle path calculator 54 receives the sequential density estimates for the projected path and several alternative adjacent paths, it can select the one that poses the least hazard and resistance to needle insertion. For example the needle path calculator can select the sequence of densities with the lowest peak density. Or, the needle path calculator can sum or average the sequential density values of each path and select the one with the lowest combined or average density. The coordinates of one or more alternative paths which have been identified as more favorable for needle insertion are then coupled to the graphics generator for indication on the displayed image.

Figure 4:
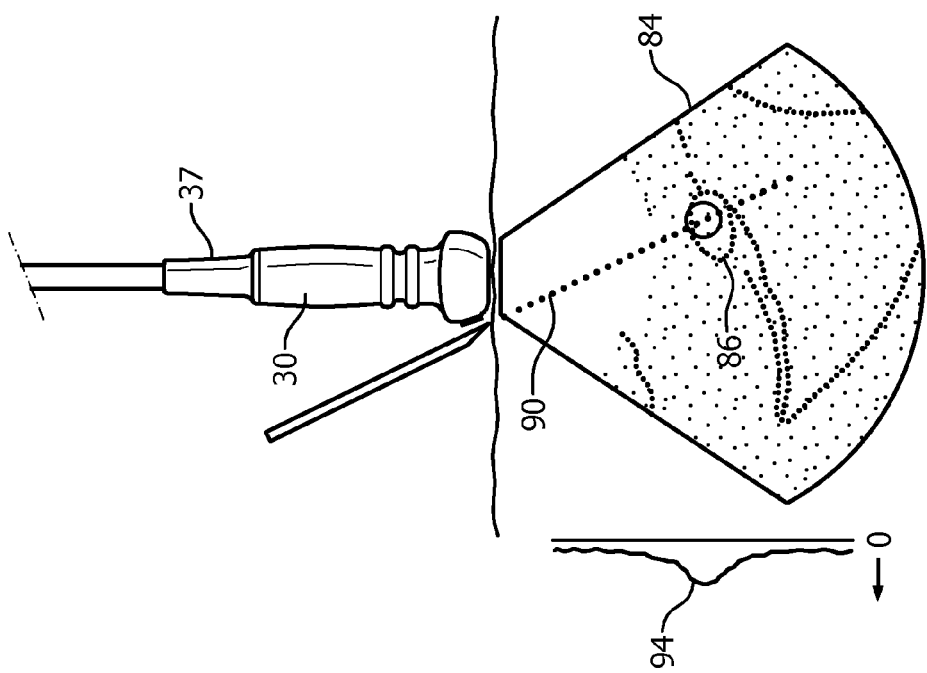
FIG. 4 illustrates the positioning of a needle for a biopsy procedure and a projected path of insertion.

A procedure conducted in accordance with the present invention can proceed as follows. The clinician hold an ultrasound imaging probe 30 by its handle 40 and places the distal end of the probe 32 which contains the transducer array in contact with the surface 80 of a body. With acoustic contact with the skin established the probe will image the interior of the body as illustrated by the 2D sector region 84 which is shown to contain the ultrasound image. The region of the body which is imaged contains target tissue 86 which is to be biopsied. The clinician manipulates a target icon control of the control panel 20 to position a target graphic over the target tissue in the image as shown by the circle graphic 92 in FIG. 4. The navigation system identifies the position of the circle graphic in the image 84 and, using the the coordinates of the position and orientation of the needle in the electromagnetic field, produces a graphic 90 on the ultrasound image which predicts the insertion path of the needle 60. As FIG. 4 illustrates, the projected path of the needle 60 in this example is graphically identified by a line of dots 90 in line with the needle 60 and the target graphic 92. When the clinician continues to insert the needle in this orientation, the path of the needle will follow the line of dots 90 and reach the target tissue identified by the target graphic 90.

Figure 5:
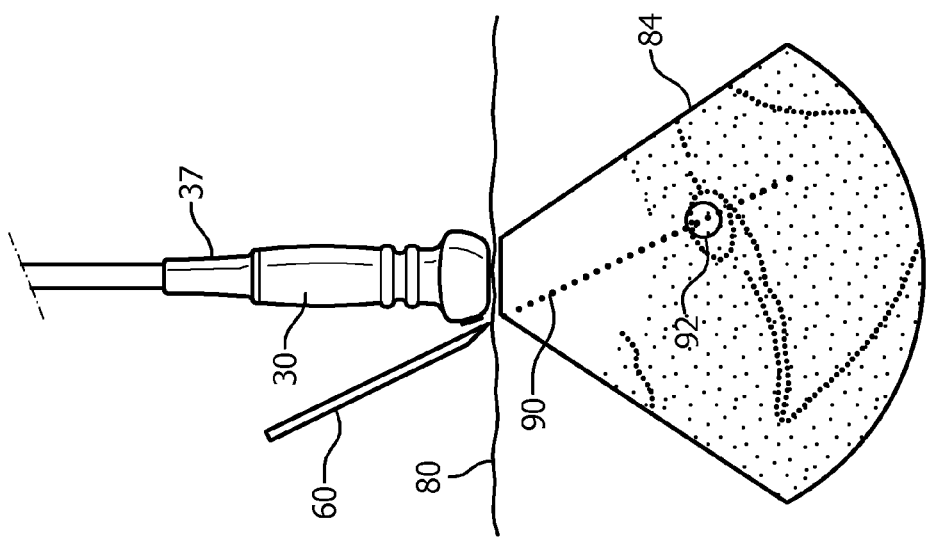
FIG. 5 illustrates the imaging state of FIG. 4 with an indication of tissue density along the projected path of insertion.
Figure 7:
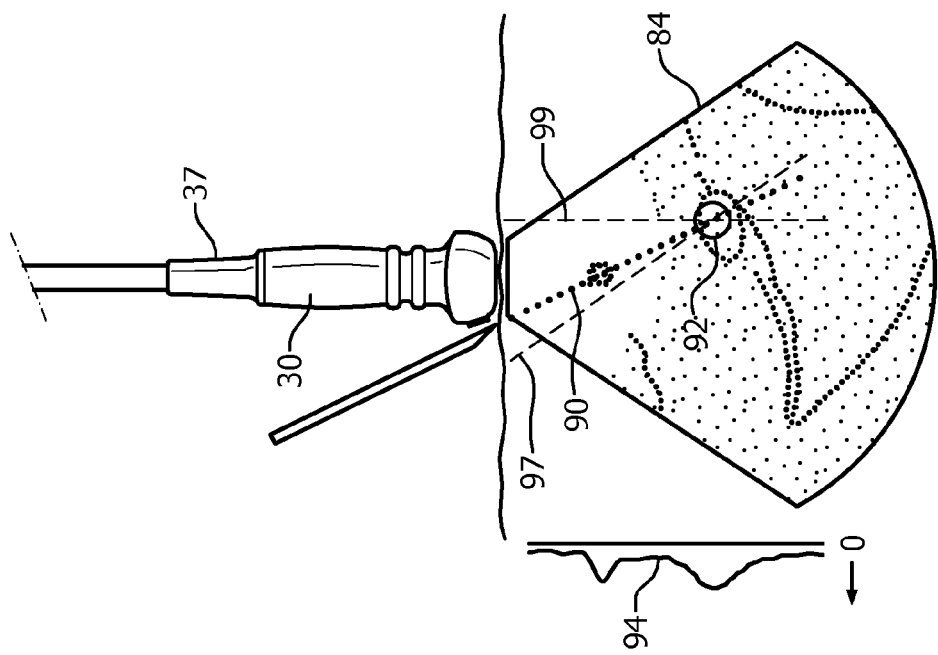
FIG. 7 illustrates the imaging state of FIG. 6 with suggested alternative paths of insertion.

With the projected needle path now identified by the line of dots 90, the tissue density analyzer 52 can access the pixels along the projected path and analyze them to determine tissue density along the path. In the example of FIG. 5 the needle path calculator has caused the sequence of density estimates along the path to be graphically displayed as a curve 94 in relation to a zero baseline. In this example the curve 94 shows the tissue density to be relatively low and substantially uniform from a shallow depth to the target tissue 86, where the solid mass of the target tissue has caused a noticeable increase of the density curve 94. The clinician may be satisfied with these characteristics of the tissue along the projected path of insertion and may then insert the needle along the line of dots 90 to biopsy the mass 86.

Figure 6:
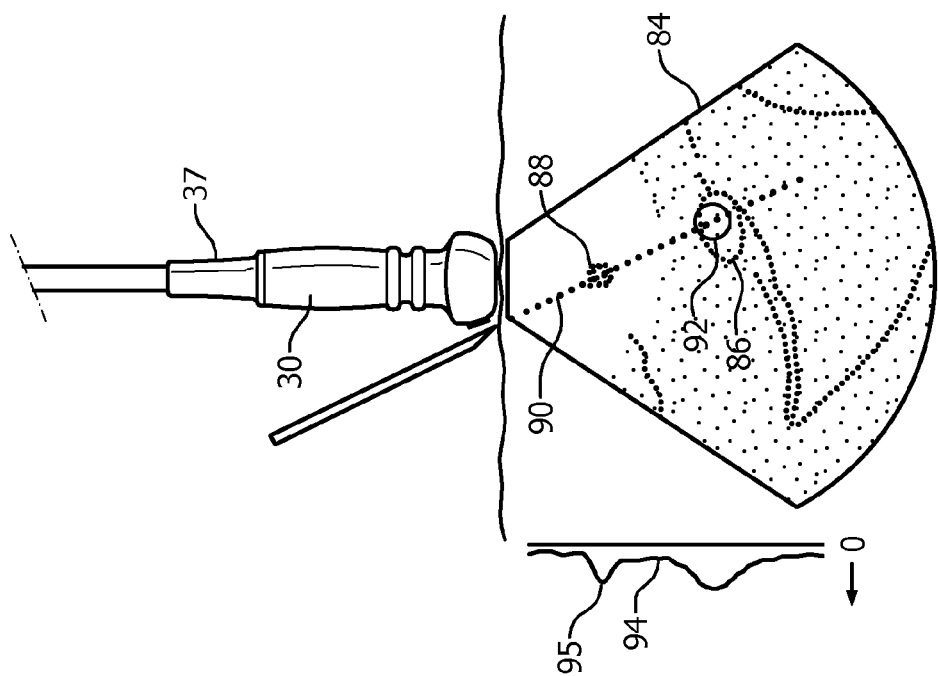
FIG. 6 illustrates the imaging state of FIG. 4 with a dense anatomical structure in the projected path of needle insertion.

FIG. 6 illustrates a different situation, in which there is a semi-solid mass 88 such as a cyst in the needle insertion path. When the tissue density analyzer and the needle path calculator generate a curve for this insertion path, the curve 94 is seen to have a second peak 95 indicating the greater density in the path posed by the cyst 88. In this example the clinician decides that the insertion path proposed by the dots 90 is unacceptable and queries the system to propose a more desirable insertion path. The clinician actuates a control on the control panel 20 which causes the tissue density analyzer and needle path calculator to iteratively identify, analyze, and propose alternative insertion paths, as described above. In this example the needle path calculator has found and identified two alternative insertion paths which are graphically indicated by dashed lines 97 and 99 on the ultrasound image. The proposed insertion path 97 is tilted slightly to the left of the current insertion path 90, and the proposed insertion path 99 is located to the right of the current insertion path and accessed from the other side of the probe 30. When the clinician moves or reinserts the needle tip in line with one of these alternative insertion paths, the navigation system causes the line of dots 90 to move in line with the proposed path, and the density curve 94 will change and display density along the newly aligned path. The clinician can then choose the insertion path that is deemed to be most appropriate to perform the biopsy procedure.

While the above examples illustrate the display of a tissue density curve 94, the display of the curve can be omitted in a constructed embodiment. The system will then only show alternative insertion paths. Another possible implementation is to illustrate the tissue density along an insertion path by a numeric value such as the average or peak or mean value of the sequence of density values. Yet another possibility is to omit the proposed insertion lines 97 and 99 and just show the density curve or value of the dotted insertion path in line with the needle as the needle is moved to various possible insertion positions. A clinician may also prefer to employ a needle guide to aid in guiding the needle insertion. As a needle is inserted, the system can monitor the path of insertion, compare it with a recommended insertion path, and advise the clinician as to whether the prescribe path is being followed or that the insertion is varying from the prescribed path. Other variations from the examples described above will be readily apparent to those skilled in the art.

What is claimed is:

1. An ultrasonic imaging system which visually guides the insertion of an invasive device such as a needle, the system comprising:
    an ultrasound probe having an array transducer for imaging a region of tissue containing target tissue and producing received signals;
    one or more processors configured by machine-readable instructions to:
        process signals received by the ultrasound probe to produce a set of spatially identified pixels having pixel values proportionate to the received signals;
        produce an ultrasound image based on the pixel values;
        produce an estimate of tissue density based on the pixel values of spatially identified pixels corresponding to a path of invasive device insertion; and
        calculate a path of invasive device insertion based on the estimate of tissue density prior to insertion of the invasive device; and
    a display configured to display the ultrasound image, the estimate of tissue density, and the calculated path of invasive device insertion, wherein the display is configured to display the calculated path of invasive device insertion in spatial registration with the ultrasound image.

2. The ultrasonic imaging system of claim 1, wherein the display is further configured to display the estimate of tissue density as a curve of relative tissue density along the path of invasive device insertion.

3. The ultrasonic imaging system of claim 1, wherein the display is further configured to display the estimate of tissue density numerically.

4. The ultrasonic imaging system of claim 1, further comprising a spatial navigation system which identifies the position and orientation of a needle in relation to the target tissue,
    wherein the navigation system is operable to identify a projected path of needle insertion in relation to the position and orientation of the needle, and
    wherein the display is further configured to display the projected path of needle insertion in spatial registration with the ultrasound image.

5. The ultrasonic imaging system of claim 4, wherein the one or more processors are further configured to produce an estimate of tissue density along the projected path of needle insertion using the values of pixels in registration with the projected path.

6. The ultrasonic imaging system of claim 1, wherein the ultrasound image further comprises a 2D ultrasound image; and wherein the one or more processors are configured to produce the estimate of tissue density using the values of pixels of the 2D ultrasound image.

7. The ultrasonic imaging system of claim 1, wherein the array transducer further comprises a 2D array transducer used by the probe to scan a volumetric region of tissue;

wherein the volumetric region includes a plane of a 2D ultrasound image; and wherein the one or more processors are configured to produce the estimate of tissue density using a group of pixels representing a three dimensional region.

8. The ultrasonic imaging system of claim 7, wherein some of the pixels of the group are coincident with the plane of the 2D ultrasound image.

9. The ultrasonic imaging system of claim 7, wherein the one or more processors are further configured to produce a sequence of tissue density estimates along a path of needle insertion, wherein each estimate is produced from a two dimensional array of pixels having at least two pixels in each of the dimensions.

10. The ultrasonic imaging system of claim 1, wherein the one or more processors are further configured to:

produce estimates of tissue density along a plurality of possible paths of needle insertion, and calculate a plurality of proposed paths of needle insertion, wherein the display is further configured to display one of the proposed paths in spatial registration with the ultrasound image.

11. The ultrasonic imaging system of claim 10, wherein the display is further configured to display the plurality of proposed paths in spatial registration with the ultrasound image.

12. The ultrasonic imaging system of claim 1, wherein the one or more processors are further configured to produce graphics such that the ultrasound image is overlaid with the graphics, wherein the graphics comprise a path of needle insertion.

13. The ultrasonic imaging system of claim 12, further comprising a user control which is actuated to indicate the location of a target tissue in the ultrasound image, wherein the one or more processors are further configured to produce a target tissue graphic in registration with the ultrasound image based on the indicate the location of a target tissue by the user control.

14. The ultrasonic imaging system of claim 12, wherein the one or more processors are further configured to:

calculate a path of needle insertion based on the estimate of tissue density, and produce a graphic representing a proposed path of needle insertion based on the calculated path of needle insertion.

15. The ultrasonic imaging system of claim 1, wherein the calculated path of invasive device insertion indicates a path that poses the least hazard and resistance to invasive device insertion.

* * * * *